United States Patent [19]

Lam

[11] Patent Number: 4,595,095

[45] Date of Patent: Jun. 17, 1986

[54] CASE FOR JEWELRY AND/OR GEMSTONES

[76] Inventor: Philip Y. T. Lam, P.O. Box 96259 T.S.T., Room 1107, Hong Shing Bldg., 363-373 Nathan Rd., Kowloon, Hong Kong

[21] Appl. No.: 633,951

[22] Filed: Jul. 24, 1984

[51] Int. Cl.⁴ ..................... B65D 25/54; B65D 61/00; A45C 11/16

[52] U.S. Cl. ............... 206/45.34; 206/45.19; 220/82 A

[58] Field of Search ................. 206/45.34, 45.19, 0.82, 206/0.83, 583, 459; 220/82 A

[56] References Cited

U.S. PATENT DOCUMENTS

| | | | |
|---|---|---|---|
| 2,144,336 | 1/1939 | Katz | 206/45.19 |
| 2,313,766 | 3/1943 | Pfanstiehl | 206/45.19 |
| 2,681,142 | 6/1954 | Cohen | 206/583 |
| 3,139,977 | 7/1964 | Burdick | 206/0.82 |
| 3,406,821 | 10/1968 | Weissberg | 206/45.34 |
| 4,275,810 | 6/1981 | Waldmeier | 206/45.34 |
| 4,320,831 | 3/1982 | Szabo et al. | 206/45.34 |
| 4,364,472 | 12/1982 | Waldmeier | 206/45.34 |

FOREIGN PATENT DOCUMENTS

| | | |
|---|---|---|
| 219018 | 12/1924 | United Kingdom . |
| 312009 | 5/1929 | United Kingdom . |
| 340250 | 12/1930 | United Kingdom . |
| 737832 | 10/1955 | United Kingdom . |
| 1383601 | 2/1975 | United Kingdom . |

Primary Examiner—William Price
Assistant Examiner—Brenda J. Ehrhardt
Attorney, Agent, or Firm—Renner, otto, Boisselle & Lyon

[57] ABSTRACT

A case for jewels and/or gemstones comprises a bottom case portion, an upper case portion and a holder for holding the case portions together, the holder being provided with a locking device. The case portion is provided with support plates for holding the jewels and/or gemstones and one plate is urged towards the other plate by a layer of resilient foam material and held by a wire spring.

10 Claims, 11 Drawing Figures

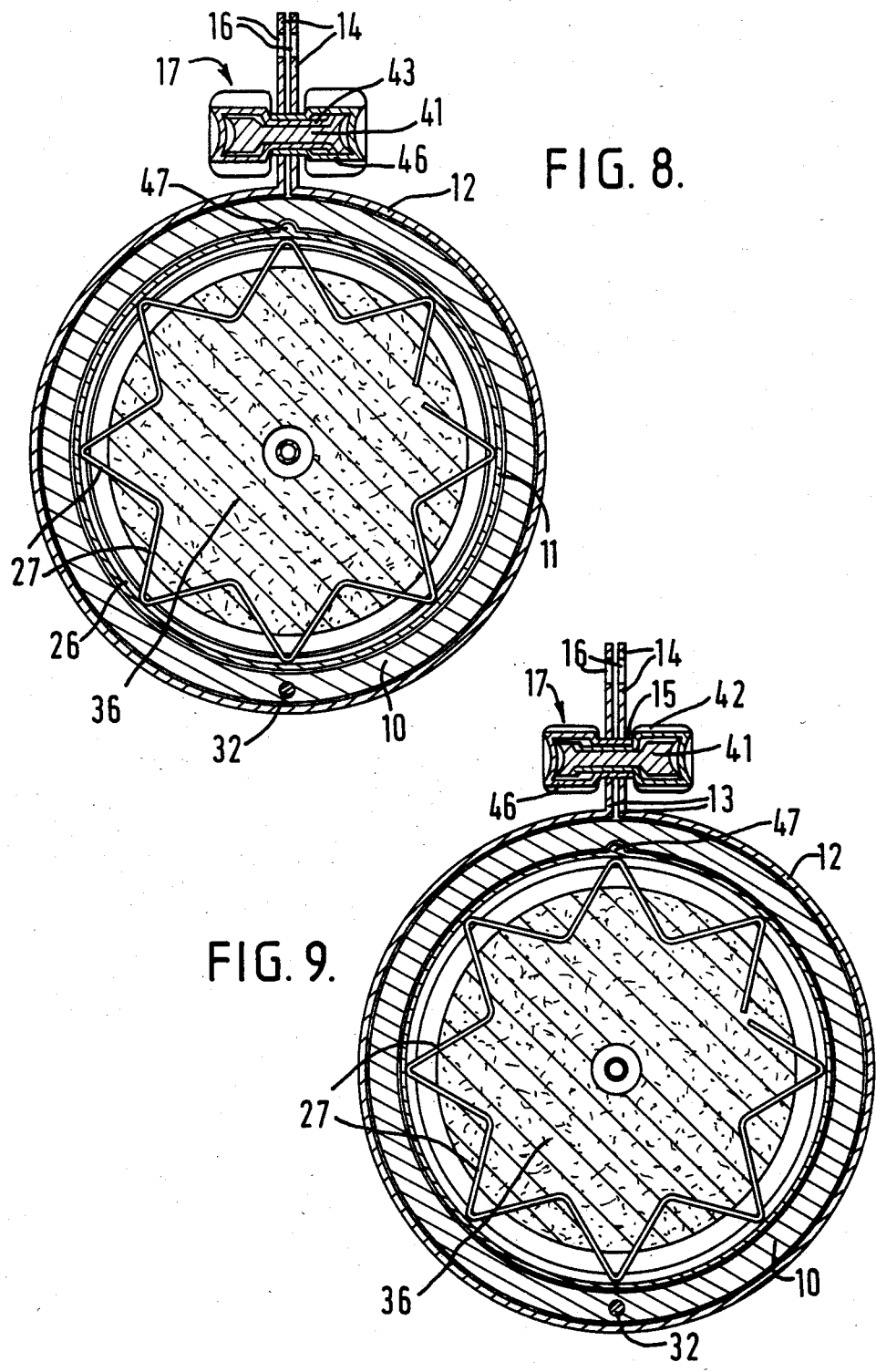

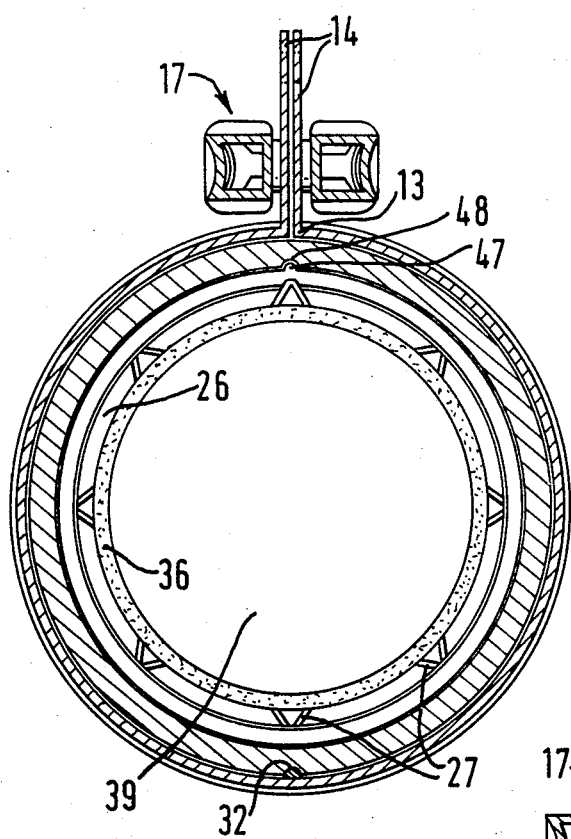
FIG. 10.
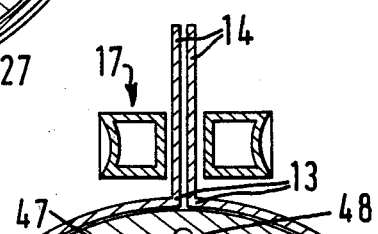
FIG. 11.
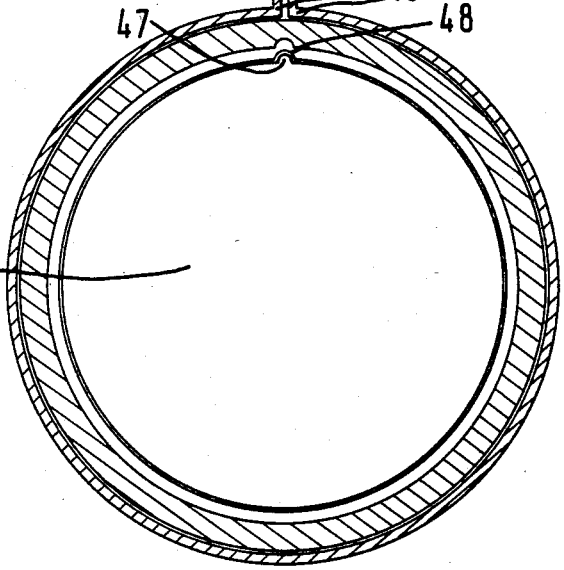

CASE FOR JEWELRY AND/OR GEMSTONES

SUMMARY OF THE INVENTION

This invention relates to a case for jewellery and/or valuable gemstones.

According to the present invention there is provided a case for jewels and/or gemstones comprising a bottom case portion, an upper case portion, a holder surrounding the peripheries of the case portions for holding the case portions together and locking means for locking the holder in its operative condition, said upper case portion being provided internally with plates for supporting jewels and/or gemstones.

BRIEF DESCRIPTION OF THE DRAWINGS

To the accomplishment of the foregoing and related ends, the invention then comprises the features hereinafter fully described and particularly pointed out in the claims, the following description and annexed drawings setting forth in detail an illustrative embodiment of the invention, this being indicative however of only one in which the principle of the invention may be employed.

In said annexed drawings:

FIG. 8 is a section taken along the line 8—8 of FIG. 5,

FIG. 9 is a section taken along the line 9—9 of FIG. 5,

FIG. 10 is a section taken along the line 10—10 of FIG. 5, and

FIG. 11 is a section taken along the line 11—11 of FIG. 5.

DESCRIPTION OF THE PREFERRED EMBODIMENTS

Figure 1:
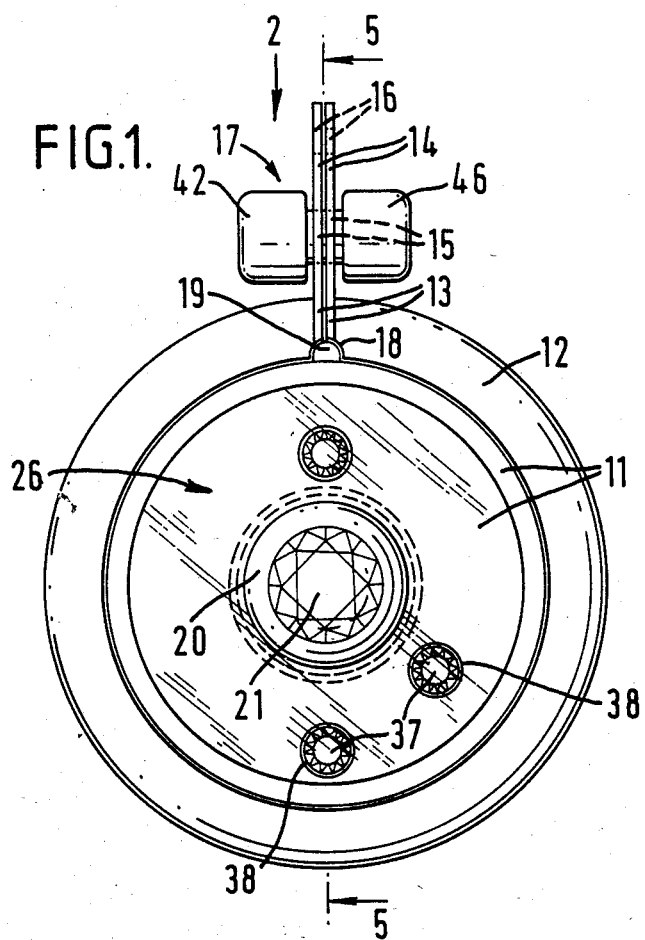
FIG. 1 is a plan view of a case according to the present invention.
Figure 2:
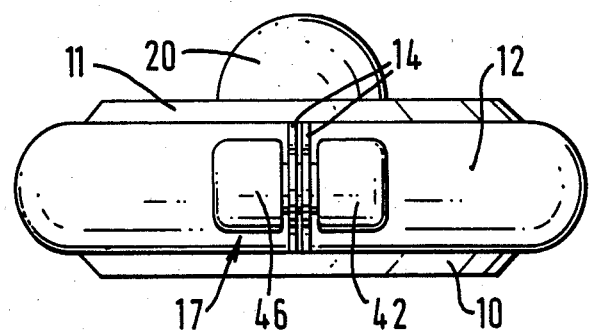
FIG. 2 is a side view taken in the direction of arrow 2 of FIG. 1.
Figure 3:
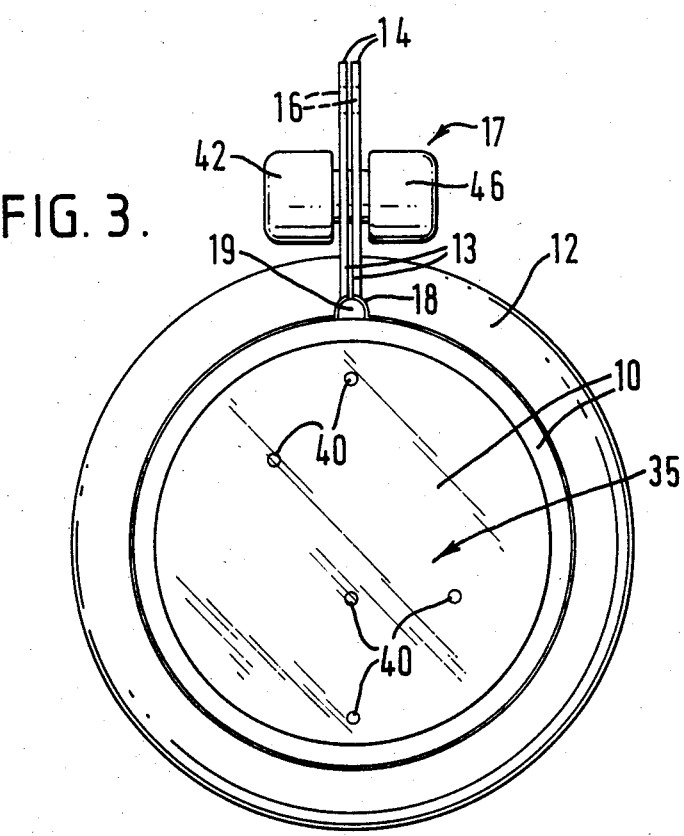
FIG. 3 is a bottom view of the case.
Figure 4:
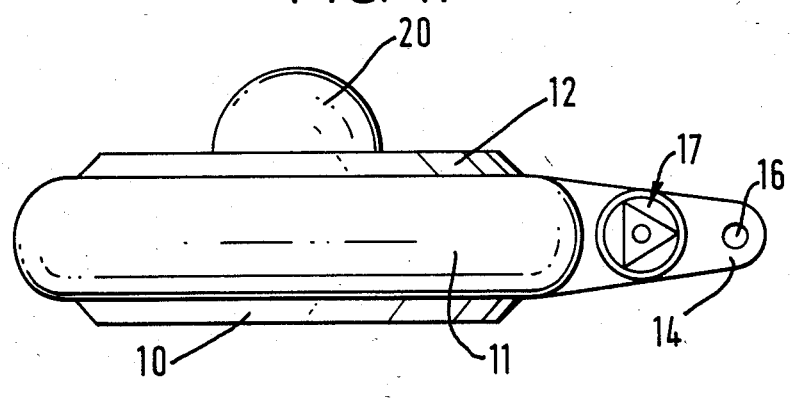
FIG. 4 is a side view taken in the direction of arrow 4 of FIG. 1.
Figure 5:
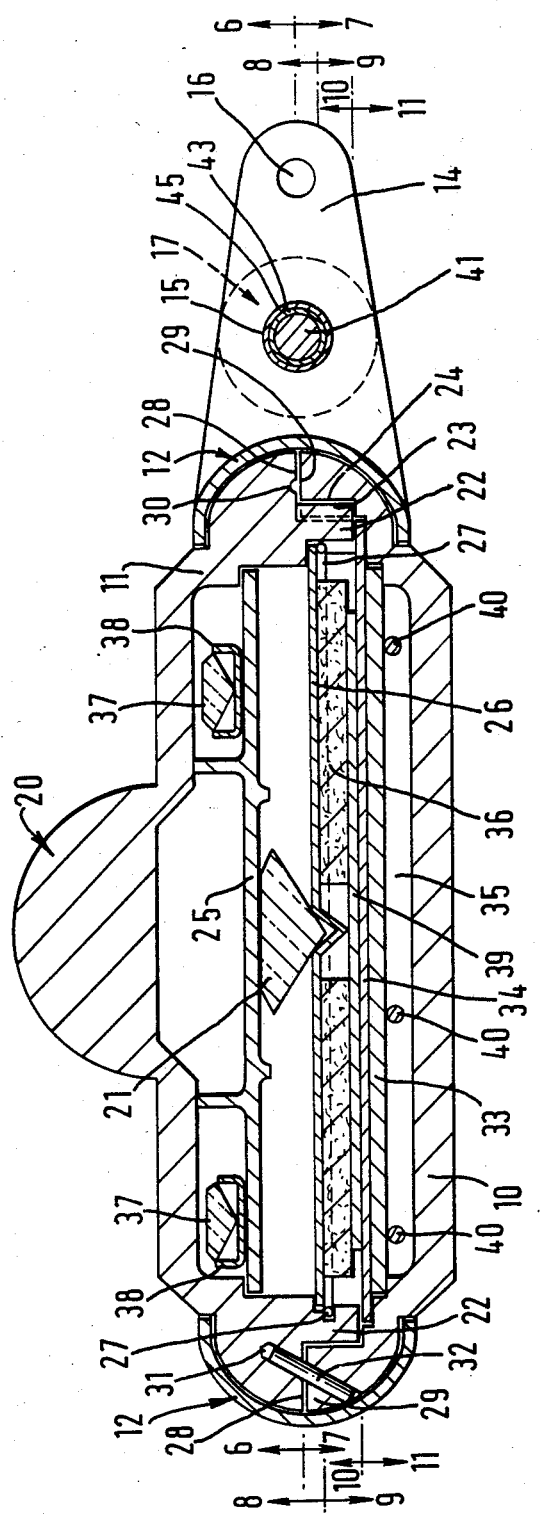
FIG. 5 is a section taken along the line 5—5 of FIG. 1.
Figure 7:
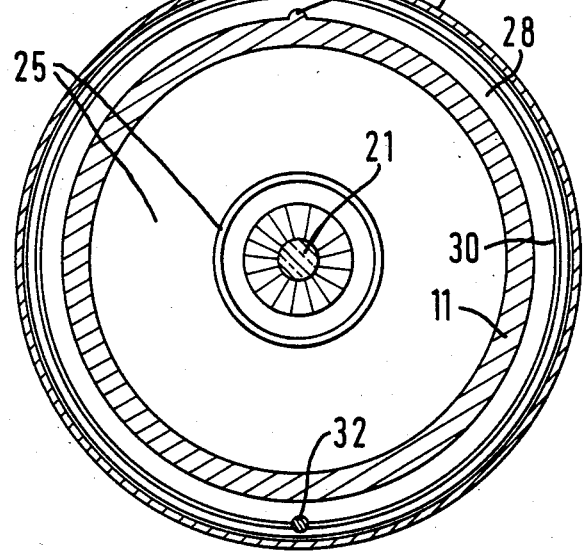
FIG. 7 is a section taken along the line 7—7 of FIG. 5.
Figure 6:
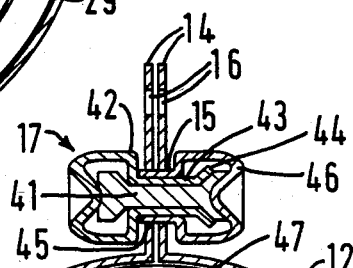
FIG. 6 is a section taken along the line 6—6 of FIG. 5.

The case comprises a bottom case portion 10 which is circular in plan view, an upper case portion 11 which is also circular in plan view, and a holder 12 in the form of a band which extends around the peripheries of the case portions 10 and 11.

The holder 12 is formed of a non-transparent non-magnetic hard material, such as a metal. It is substantially circular in plan view and has ends 13 which extend radially outwardly forming a pair of flanges 14. In transverse cross-section the body of the holder 12 is part circular. The flanges 14 are each provided with holes 15 and 16. The holes 15 are for the provision of a locking device 17 and the holes 16 enable the case to be linked, or hooked to another object. The external surface of the holder 12 can be engraved with a decorative pattern. When the locking device 17 is unlocked the holder 12 can be expanded by moving the flanges 14 apart so as to allow the case portions 10 and 11 to be removed from or reinserted into the holder 12. In the region of the flanges 14 the holder 12 is provided with a curved recess 18 which receives locating portions 19 provided on case portions 10 and 11.

The upper case portion 11 is formed of a transparent material so that the contents of the case can be viewed. It has a domed portion 20 which forms a magnifying lens to enlarge the main displayed object 21. The periphery of the case portion 11 is part circular in section enabling it to seat in the holder 12. The case portion 11 has an annular downwardly extending flange 22 which is provided on its outer periphery with a portion 23 which engages in a recess 24 provided on the bottom case portion 10 so that the upper case portion 11 cannot be rotated relative to the bottom case portion 10. The upper case portion 11 is stepped internally to provide support for a top transparent support plate 25 and a non-magnetic metal support plate 26 which is retained by a stainless-steel wire spring clip 27 which engages in a groove. The upper case portion 11 also has an annular face 28 against which the bottom case portion 10 seats.

The bottom case portion 10 is formed of transparent material and internally is stepped and provided with a face 29 opposed to the face 28. The face 28 is provided with a groove 30 which receives a seal or sealant material so that an air and moisture and waterproof seal is provided. After the casing portions 10 and 11 have been brought together and sealed a hole or holes 31 are drilled in the peripheral portions at a location or locations where they will be covered by the holder 12 and a magnetic pin 32 is inserted in the or each hole 31. the location angle of inclination and size of the or each hole 31 will be different for each case produced and the location, angle, size and number of holes 31, and thus pins 32, will be recorded for future identification and be given a confidential serial number for security purposes. This will enable each case to be given a security identification. The bottom case portion 11 supors a bottom transparent plate 33 and a non-magnetic steel bottom plate 34. the bottom transparent plate 33 defines with the bottom case portion 10 a sealed space 35.

The main displayed object 21 is located below the domed portion 20 and is supported by the support plate 26 and located between the support plate 26 and the plate 25. The support plate 26 is held in position by the wire spring clip 27 and provided on the underside of the support plate 26 is a layer of foamed material 36. The support plate 26 is thus upwardly biased by the foam material 36 and urges the object 21 into contact with the plate 25 so that the object 21 is held in a stable position. A description of the object 21 is provided on the underside of the bottom plate 34. Further displayed objects 37 are provided in holders 38 provided on the upper side of plate 25. The holders 38 may be fixed or they may be allowed to move freely on the plate 25. A description of the objects 37 can be provided on the underside of the bottom plate 34.

Provided between the layer of foamed material 36 and the plate 34 is a micro-film 39 of a certificate which the owner will have giving the contents, ownership details etc.

Within the space 35 are objects 40 of any desired shape or form which are movable within the space 35 and which provide a decorative appearance to the case.

The locking device 17 consists of a core or insert 41 formed of a soft metal or other suitable material which can be easily deformed. The core 41 is located within a button member 42 and extends through a stem portion 43 having a flared end 44. Mounted on the stem portion 43 is a stem portion 45 of a second button member 46. Initially the core 41, button member 42 and button member 46 are separate parts. When the flanges 14 have been brought together after the casing portions 10 and 11 have been assembled and inserted into the open holder 12, the stem 45 of button member 46 is inserted into the aligned holes 15 and the core or insert 41 inserted into the stem portion 43 and the stem 43 pushed into the stem 45. Opposed forces are then applied to the button members 42, 46, i.e. by a punch, to change the shape of the button members. Both ends of the core or insert 41 are deformed and prevent separation of the button members.

Removal of the holder 12 can only then be achieved by breaking and destroying the locking device 17, which cannot be re-used.

The plates 26 and 34 each have at their periphery a locating projection 47 which engages in a recess 48 in the respective casing portion.

The plate 33 is sealed to the bottom casing portion 10.

The items 21, 37 may be gemstones or valuable jewellery items.

I, therefore particularly point out and distinctly claim as my invention:

1. A case for jewels and/or gemstones comprising a bottom case portion, an upper case portion, a holder surrounding peripheries of the case portions for holding the case portions together and locking means for locking the holder in its operative condition, said upper case portion being provided internally with plates for supporting the jewels and/or gemstones, said plates comprising an upper plate spaced from an upper wall portion of said upper case portion and defining therewith a space in which jewel and/or gemstone items are located, and a lower plate spaced from said upper plate and defining therewith a second space in which a main jewel or gemstone is located, said lower plate being held in position by a wire retaining member engaged with the upper case portion.

2. A case as claimed in claim 1, in which the bottom case portion is provided internally with a first plate which is spaced from the lower plate of the upper case portion, a sheet of resilient material being provided between said first plate and said lower plate which biasses said lower plate towards the upper plate of the upper case portion.

3. A case as claimed in claim 2, in which the sheet of resilient material comprises a foamed material.

4. A case as claimed in claim 2 or claim 3, in which the bottom case portion is provided with a second transparent plate located beneath said first plate, said transparent plate being spaced from the bottom wall of the buttom case portion to define therewith a space in which decorative objects are located.

5. A case as claimed in any one of claim 2, in which a micro-film is located between the sheet of resilient material and said first plate of the bottom case portion.

6. A case as claimed in claim 2 or 3 in which a seal is provided between the case portions.

7. A case as claimed in claim 2 or 3, in which the upper case portion is provided with a magnifying portion for magnifying at least part of the contents of the case.

8. A case as claimed in claim 2 or 3, in which the case portions are provided with one or more holes in which a pin of magnetic material is received, said pin or pins being covered by said holder and being provided for security identification purposes.

9. A case as claimed in claim 2 or 3 in which the holder is provided with two outwardly directed flange portions having aligned holes therein for receiving the locking means.

10. A case as claimed in claim 11, in which said locking means comprises a first deformable button member having a shank portion received in a shank portion of a second deformable button member which extends through said aligned holes, a core of a deformable metal extending through the shank portion of the first button member and into the interior of the second button member and being deformed to hold the two button members together.

* * * * *